(12) United States Patent
Baxter et al.

(10) Patent No.: US 6,719,776 B2
(45) Date of Patent: Apr. 13, 2004

(54) THUMB PAD ACTUATOR FOR AN ULTRASONIC SURGICAL INSTRUMENT

(75) Inventors: Chester O. Baxter, Loveland, OH (US); Richard M. Harper, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 129 days.

(21) Appl. No.: 09/796,855

(22) Filed: Mar. 1, 2001

(65) Prior Publication Data

US 2002/0123742 A1 Sep. 5, 2002

(51) Int. Cl.[7] .................. A61B 17/28; A61B 17/42; A61B 17/44
(52) U.S. Cl. .................. 606/205; 606/169; 606/208
(58) Field of Search .................. 606/205, 144, 606/142, 41, 96, 169, 1; 227/175.2

(56) References Cited

U.S. PATENT DOCUMENTS

| 5,116,349 | A | * | 5/1992 | Aranyi | 606/142 |
| 5,762,255 | A | * | 6/1998 | Chrisman et al. | 227/175.2 |
| 5,910,148 | A | * | 6/1999 | Reimels et al. | 606/144 |
| 5,954,746 | A | * | 9/1999 | Holthaus et al. | 606/205 |

* cited by examiner

Primary Examiner—Henry Bennett
Assistant Examiner—Sabrina Dagostino
(74) Attorney, Agent, or Firm—Scully, Scott, Murphy & Presser

(57) ABSTRACT

An ultrasonic surgical instrument includes a large thumb slide actuator and a handle which is held in to the palm of a surgeon operator to balance the weight of the instrument during usage. The surgeon's thumb is placed upon the thumb slide actuator, thereby facilitating actuation with a pulling-pushing motion of the thumb slide. When the thumb slide is pushed forward in a distal direction, a rotational clamp arm is opened relative to a stationary blade, and when the thumb slide is pulled rearward in a proximal direction, the clamp arm is closed. This arrangement eliminates a problem with steadying the instrument, with the entire thumb resting on the thumb slide, and also eliminates pressure points on the thumb during long transection times. The large thumb slide features a ribbed texture on its upper surface to prevent thumb slippage. The thumb slide is optimized for ergonomic usage with all size hands, with the user being able to initiate an open or close movement from any point on the thumb slide. The thumb slide has a horizontal S shaped design which fits the normal curvature of the thumb to provide greater comfort and control. The thumb slide is actuated proximally and distally along the same arc which the thumb follows naturally when bent proximally and distally at the first knuckle, which provides the surgeon with a natural and familiar actuating movement for greater ease and control.

44 Claims, 3 Drawing Sheets

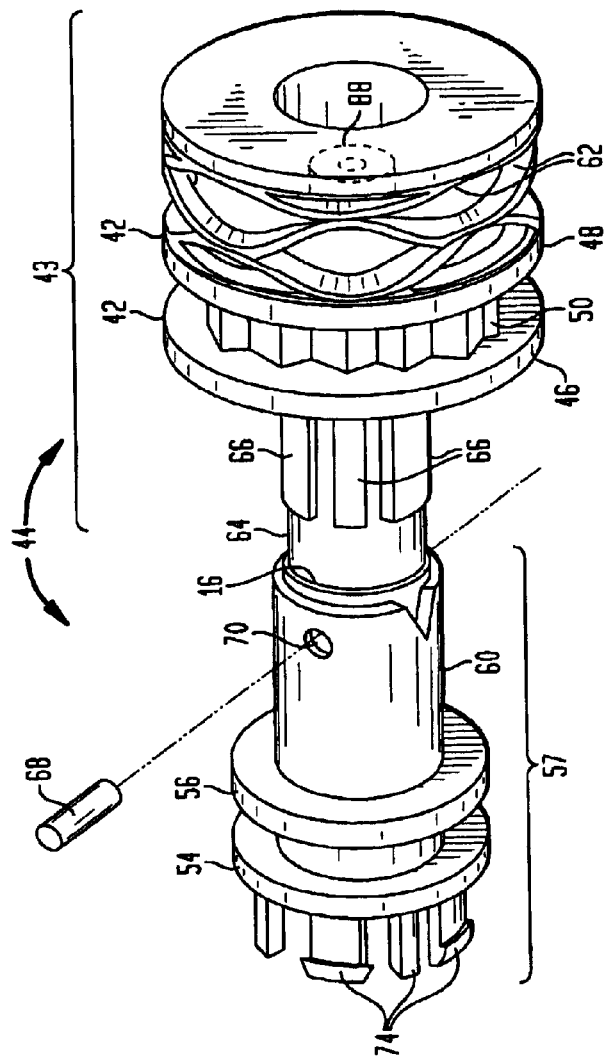
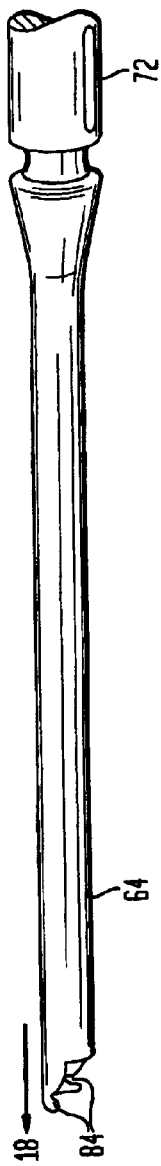

THUMB PAD ACTUATOR FOR AN ULTRASONIC SURGICAL INSTRUMENT

BACKGROUND OF THE INVENTION

1. Field of the Invention

The present invention relates generally to a thumb pad actuator for an ultrasonic surgical instrument, and more particularly pertains to a thumb pad actuator for an ultrasonic surgical instrument which is ergonomically designed to be comfortable and reduce fatigue in a surgeon's hand and arm, particularly during long procedures.

2. Discussion of the Prior Art

For a physician to perform at an optimum level, it is important that the physician have an instrument which is comfortable, reduces fatigue, and is simple to operate. A problem in the prior art is that the extant technology has not done enough to meet the ergonomic needs of the physician. The instruments presently on the market are often uncomfortable to use, especially during long procedures, and are also frequently poorly designed so as to create fatigue in the surgeon's hand and arm. The present invention provides a cost effective, easy to use instrument which fulfills all of these requirements.

SUMMARY OF THE INVENTION

Accordingly, it is a primary object of the present invention to provide a thumb pad actuator for an ultrasonic surgical instrument which includes a thumb-pad lever actuator. The thumb pad-lever is ergonomically designed for comfort and ease of usage and has a ribbed thumb pad to prevent thumb slippage. The thumb-pad lever is actuated along the same arc that the thumb naturally travels and bends in at the first knuckle, thus facilitating a coordinated, easy actuation with very little major muscle movement.

A further object of the subject invention is the provision of a very comfortable ultrasonic instrument with a large ergonomically designed thumb pad which decreases the amount of stress the physician feels at pressure points, thereby providing greater comfort to the physician during long procedures. The large thumb pad and its ribbed upper surface decrease the chances of thumb slippage during actuation. The actuating motion of the thumb pad lever is along the same arc that the thumb naturally moves when bending at the first knuckle, thereby making the actuating movement familiar and simple. Actuating the instrument by translation of the thumb along a familiar and natural arc decreases large muscle movements and enhances the fine motor skills required to perform delicate operations. By using as few muscle groups as possible, the instrument also succeeds in decreasing the fatigue of physicians operating the instrument over long periods of time.

In accordance with the teachings herein, the present invention provides an ultrasonic surgical instrument which includes a handle and a large thumb slide actuator. In usage, the handle is held in the palm of a surgeon user to balance the weight of the instrument during a surgical procedure. The user's thumb is then placed upon the thumb slide actuator, thereby facilitating actuation with a pulling-pushing motion of the thumb slide. When the thumb slide is pushed forward, a rotational clamp arm at the distal end of the instrument is opened relative to a stationary blade, and when the thumb slide is pulled rearward, the clamp arm is closed relative to the stationary blade.

This arrangement eliminates a problem with steadying the instrument, with the entire thumb resting on the thumb slide, and also eliminates pressure points on the thumb during long transection times. The large thumb slide features a ribbed texture on its upper surface to prevent thumb slippage. The thumb slide is optimized for ergonomic usage with all size hands, with the user being able to initiate an open or close movement from any point on the thumb slide. The thumb slide has a horizontal S shaped design which fits the normal curvature of the thumb to provide greater comfort and control. The thumb slide is actuated proximally and distally along the same arc which the thumb follows naturally when bent proximally and distally at the first knuckle, thereby providing the surgeon with a natural and familiar actuating movement for greater ease and control.

BRIEF DESCRIPTION OF THE DRAWINGS

The foregoing objects and advantages of the present invention for a thumb pad actuator for an ultrasonic surgical instrument may be more readily understood by one skilled in the art with reference being had to the following detailed description of several preferred embodiments thereof, taken in conjunction with the accompanying drawings wherein like elements are designated by identical reference numerals throughout the several views, and in which:

FIG. 2 is a side perspective view of a rotational coupler which is rotationally mounted within the housing body of the surgical instrument, while also coupling an actuating translating movement of the thumb pad actuator to a rotational movement of a clamp arm relative to a blade at the distal end of the surgical instrument.

FIG. 3 is a side perspective view of an inner actuating tube which is mounted for distal and proximal translational movements within the outer support tube, to cause the clamp arm to rotate open, or to rotate to a closed position, relative to the fixed blade.

DETAILED DESCRIPTION OF THE DRAWINGS

Figure 1:
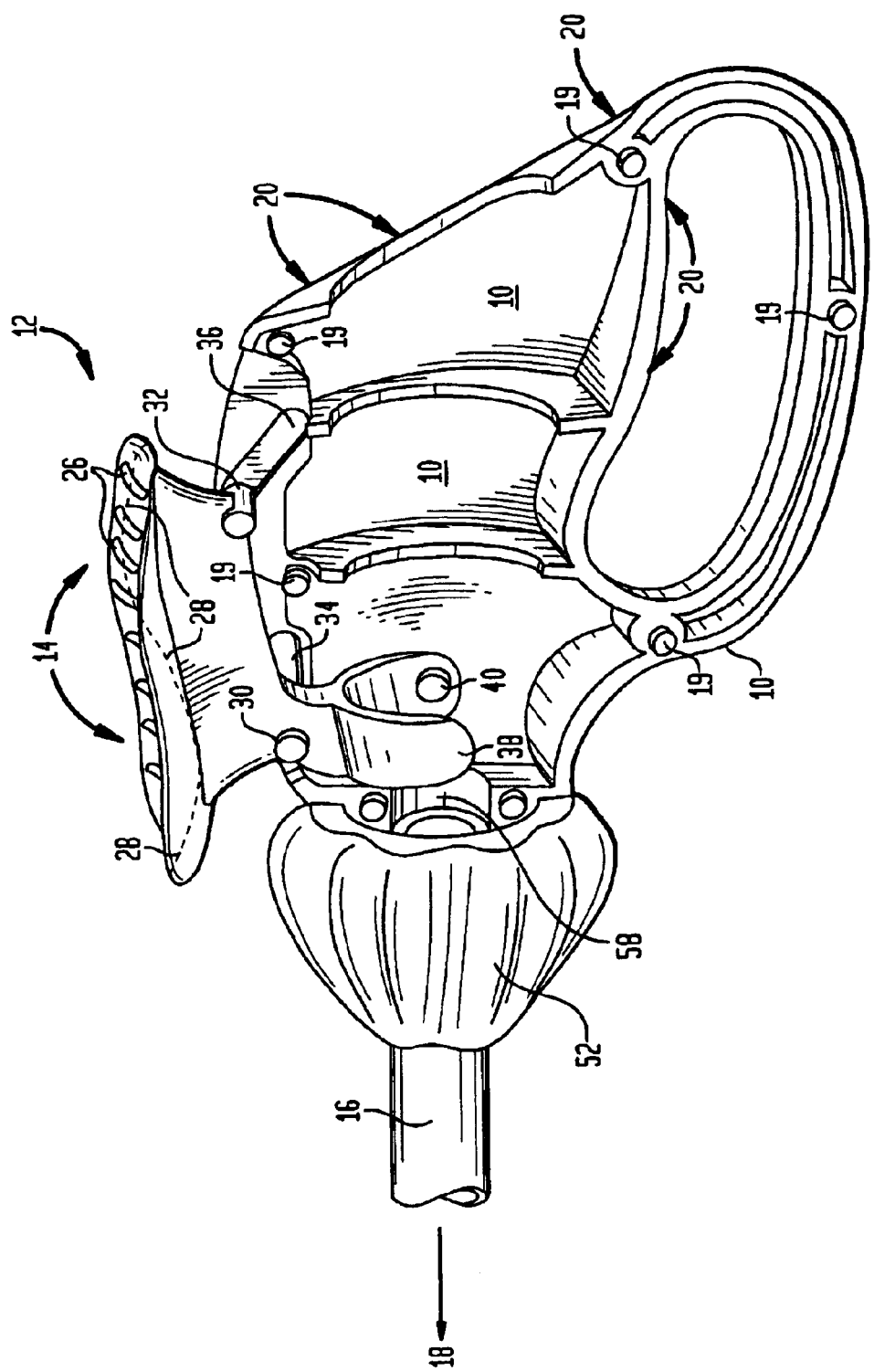
FIG. 1 is a side perspective view of the inside of one half of a housing body shroud of a surgical instrument, and illustrates the slideable mounting therein of a slideable thumb pad actuator, and an outer support tube extending towards the distal end of the surgical instrument.

Referring to the drawings in detail, FIG. 1 is a side perspective view of the inside of one half of a major housing body shroud 10 of a surgical instrument 12, and illustrates the slideable mounting therein of a slideable thumb-pad actuator 14, and an outer support tube 16 extending towards the distal end 18 of the surgical instrument 12. The housing body is constructed from two substantially identical housing body halves 10 as shown in FIG. 1, which are secured in alignment with each other by a plurality of matrix bosses 19.

The shapes of the shrouds 10 of the ultrasonic surgical instrument 12 define a handle portion 20, and the instrument is provided with a large thumb slide actuator 14 on a top surface thereof. In usage, the handle 20 is held close to the palm of a surgeon user to balance the weight of the instrument during usage. The user's thumb is placed upon the thumb slide actuator 14, thereby facilitating actuation with a pulling-pushing motion of the thumb slide 14. When the thumb slide is pushed forward in a distal direction, a rotational curved clamp arm 22, FIGS. 4 and 5, at the distal end 18 of the instrument is opened relative to a stationary curved blade 24, and when the thumb slide 14 is pulled rearward in a proximal direction, the clamp arm 22 is closed.

This arrangement eliminates a problem of steadying the instrument, with the entire thumb resting on the thumb slide 14, and also eliminates pressure points on the thumb during long transection times. The large thumb slide 14 features a ribbed texture 26 on its upper surface to prevent thumb slippage. The thumb slide is optimized for ergonomic usage with all size hands, with the user being able to initiate an open or close movement from any point on the thumb slide. The center of the top surface of the thumb slide has a horizontal S shaped design, illustrated by dashed line 28, which fits the normal curvature of the thumb to provide greater comfort and control. The thumb slide is actuated proximally and distally along the same arc that the thumb follows naturally when bent proximally and distally at the first knuckle, which provides the surgeon with a natural and familiar actuating movement for greater ease and control.

The thumb-pad actuator 14 is mounted on top of the surgical instrument for distal and proximal movements by first and second slide pins 30 and 32 which are mounted for distal and proximal movements in first and second slide grooves 34 and 36 defined in opposed body half shrouds 10 of the surgical instrument. The first slide pin 30 is mounted on the distal end of the thumb pad actuator 14, and the second slide pin 32 is mounted on the proximal end of the thumb pad actuator 14. The first slide groove 34 extends distally and proximally in a generally horizontal direction, while the second slide groove 36 extends distally and proximally in both a generally horizontal direction and also a rearward-downwardly extending direction, such that movement of the thumb-pad actuator as guided by the first and second slide grooves 34,36 follows the natural movement of an extending and retracting thumb of a surgical operator. The distal and proximal movements of the first and second slide pins 30,32 is limited by the ends of the respective first and second grooves 34,36.

The thumb-pad actuator 14 extends downwardly at its distal end in a wishbone construction having downwardly-depending spaced-apart resilient wishbone legs 38, each of which supports an inwardly projecting drive pin 40, which are designed to be positioned on opposite sides of a tubular collar 42, FIG. 2, on a proximal translationally-movable portion 43 of a rotational coupler 44. The tubular collar 44 includes first and second spaced annular collar retainers 46,48 which extend circumferentially around the translationally-immovable proximal portion 43 of the rotational coupler to retain the drive pins 40 therein, and a series of ridged detents 50 is defined between the collar retainers 46,48 which also extend circumferentially around the rotational coupler to provide a positive detent action against the resiliently mounted drive pins 40 during rotation of the rotational coupler. The thumb pad actuator 14 can be formed of a suitable molded plastic.

Figure 5:
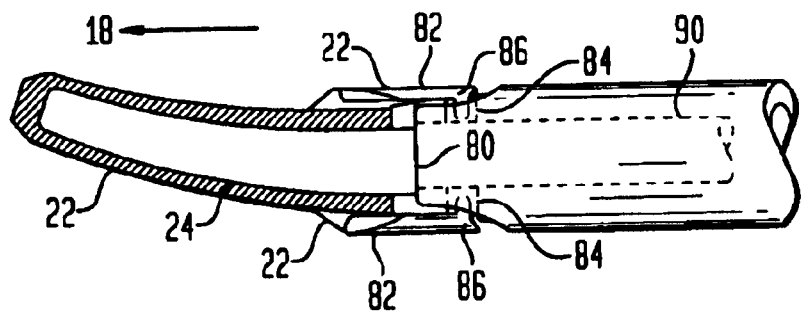
FIG. 5 is a top planar view of the distal end of the surgical instrument, and illustrates opposed side pivotal mountings in the distal end of the inner actuating tube of the clamp arm, which is pivotally controlled by distal and proximal translations of the inner actuating tube.

FIG. 1 also illustrates a distally-extending, rotationally-mounted outer knob 52 which is mounted on the distal end of the rotational coupler 44, and which allows the surgeon user to rotate the angular position of the angularly extending and offset, as shown in FIG. 5, clamp arm 22 and blade 24.

Each of the distal ends of the first and second body shrouds 10 defines half of an annular retainer ring, not shown, which is positioned between the first and second annular collar retainers 54,56 on a distal translationally-immovable portion 57 of the rotational coupler 44, to secure the translationally-immovable portion 57 of the rotational coupler 20 within the housing against translational movements in a longitudinal direction, while providing 360° angular rotational movement and freedom for the rotational coupler 44 within the instrument in the housing.

FIG. 2 is a side perspective view of the rotational coupler 44 which is mounted within the housing body half shrouds 10,10 of the surgical instrument to provide complete rotational freedom for the rotational coupler 44 and the clamp 22 and blade 24, while also serving to couple an actuating translational movement of the thumb pad actuator 14 to an actuating rotational movement of the clamp arm 22 relative to the fixed blade 24 fixedly mounted at the distal end of the outer support tube 16 at the distal end of the surgical instrument.

The rotational coupler 44 is also rotationally mounted within the instrument by a bearing sleeve 58 on each of the half shrouds 10 which rotationally encompass a cylindrical sleeve 60 of the rotational coupler, while providing for complete rotational freedom thereof within the surgical instrument. The two bearing sleeves 58 also function to secure a pin 68 in place under the two bearing sleeves 58.

A plurality of Belleville washer springs 62 are provided at the proximal end of the rotational coupler 44 to absorb extra force and travel applied by the thumb pad actuator 14 through wishbone 38, drive pins 40 and tubular collar 44, with the Belleville washer springs 62 being compressed after the clamp arm 22 is closed against the blade 24.

The translationally-immovable distal portion 57 of the rotational coupler 44, including components 54, 56, 60 and 74, is positioned around the proximal end of the outer support tube 16, as illustrated in FIG. 2, and the shaft of an inner actuating tube 64 is slideably positioned within the outer support tube 16, as illustrated in FIG. 2 and described in greater detail hereinbelow.

The translational-movable portion 43 of the rotational coupler 44 includes a plurality of longitudinally extending prongs 66 which mount around and surround the proximal end of the inner actuating tube 64, securing the two components together for both rotational and longitudinal movements.

A pin 68 extends through diametrically-opposed holes 70 in the cylindrical sleeve 60 of the translational-immovable portion 57 of the rotational coupler, through aligned diametrically-opposed holes in the proximal end of the outer support tube 16, and also through aligned diametrically-opposed longitudinally-extending slots 72 spaced from the proximal end of the inner actuating tube 64 and passes through an acoustic waveguide 90, such that the translationally-immovable portion 57 of the rotational coupler and the outer support tube 16 are locked together by the pin 68 for common rotational movements, but prevented from translational movements.

Translational movement of the tubular collar 42 caused by actuation of the thumb pad actuator 14 results in translational movement of the inner actuating tube 64 in the outer support tube 16, with the elongated slots 72 moving relative to the stationary pin 68 until the ends of the elongated slots 72 contact the pin 68. The longitudinal translational movements of the inner tube 64 within the outer support tube 16 results in opening or closing the rotationally-mounted clamp arm 22 relative to the end blade 24 which is fixedly mounted to the distal end of the outer support tube 16.

FIG. 2 also illustrates longitudinally extending prongs 74 at the distal end of the rotational coupler 44. The rotational knob 52, FIG. 1, is positioned around and locks onto the prongs 74, such that the rotational knob 52 and the angular-offset extending clamp arm 22 and end blade 24, see FIG. 5, can be rotated by the surgical operator to rotate the entire rotational coupler 44 and the attached angularly-offset clamp arm 22 and blade 24 to any selected angular position relative to the surgical instrument.

Figure 4:
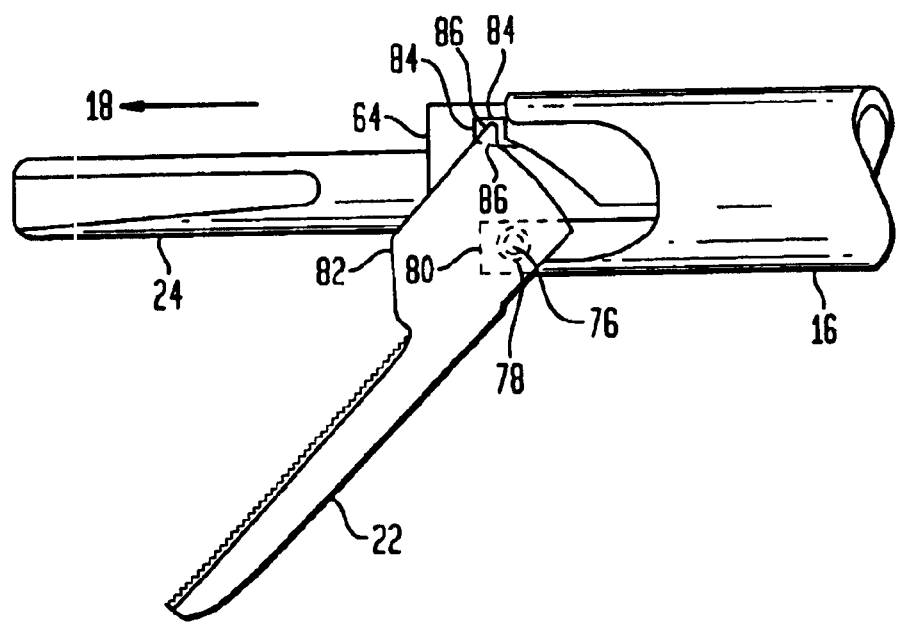
FIG. 4 is a side elevational view of the distal end of the surgical instrument, and illustrates the rotationally mounted clamp arm, which is rotated relative to a fixed blade responsive to linear movements of the thumb pad actuator.

FIG. 4 is a side elevational view of the distal end of the surgical instrument, and illustrates the rotationally mounted clamp arm 22, which is actuated by linear movements of the thumb pad actuator 14 and inner actuating tube 64, such that the clamp arm 22 is rotated open or closed relative to the fixed blade 24.

FIG. 4 illustrates two inwardly-projecting, diametrically-opposed pivot mount pins 76 on the moveable clamp arm 22 rotationally mounted within diametrically-opposed apertures 78 on opposite sides of the distal end 80 of the outer support tube 16. The distal end 80 projects along the bottom (as viewed in FIG. 4) to an end position which is covered by a substantially cylindrically shaped proximal end 82 of the clamp arm 22, which is open at the top as illustrated in FIG. 4. The arrangement is such that the clamp arm 22 can rotate relative to the lower end portion of the outer support tube 16 and the blade 24 which is fixedly mounted at the distal end of the outer support tube 16.

FIG. 3 is a side perspective view of the inner actuating tube 64 which is mounted for distal and proximal translational movements within the outer support tube 16, to cause the clamp arm 22 to rotate to an open position or to rotate to a closed position relative to the fixed blade 24. A pair of diametrically-opposed coupling slots 84, shown best in FIG. 4, at the distal end of the inner actuating tube 64 couple to receive a pair of diametrically-opposed, inwardly-extending angularly projecting legs 86, shown in both FIGS. 4 and 5, on the proximal upper (as viewed in FIG. 4) end of the clamp arm 22, which are positioned pivotally in the slots 84 to convert translational movements of the inner actuating tube 64 to rotational movement of the clamp arm 22.

The ergonomic designs of the thumb pad actuator 14 and the instrument shroud 10 and handle 20 are chosen and designed specifically for an ultrasonic surgical instrument wherein ultrasonic vibrations are transferred through an ultrasonic waveguide to the distal end of the surgical instrument to perform a useful surgical function and procedure thereat. In the disclosed and illustrated embodiment, ultrasonic energy is introduced through a threaded coupling 88 for an acoustic waveguide, which is partially shown in phantom in FIG. 2, and is positioned centrally within the proximal portion 43 of the rotational coupler 44, into the proximal end of an acoustic waveguide 90, FIG. 5, which is positioned within the inner actuating tube 64, and is connected to the stationary blade 24 to supply ultrasonic vibrations thereto to produce a useful surgical function thereat.

While several embodiments and variations of the present invention for a thumb pad actuator for an ultrasonic surgical instrument are described in detail herein, it should be apparent that the disclosure and teachings of the present invention will suggest many alternative designs to those skilled in the art.

What is claimed is:

1. An ultrasonic surgical instrument which is ergonomically designed to be comfortable and reduce fatigue in a surgeon operator's hand and arm, comprising:
   a. a housing body shroud for the ultrasonic surgical instrument which defines a handle which is held in the palm of a surgeon user to balance the weight of the instrument during usage;
   b. a thumb pad actuator translationally mounted on the upper surface of the body shroud for distal and proximal movements along substantially the same arc that the thumb naturally follows when bending proximally and distally at the first knuckle, thereby providing an actuating movement by the thumb along a familiar and natural arc which facilitates a coordinated easy actuation with very little major muscle movement;
   c. an ultrasonic waveguide for transferring ultrasonic vibrations to the distal end of the surgical instrument to perform a useful surgical procedure thereat;
   d. wherein a clamp arm is rotationally mounted relative to a blade which is stationarily supported at the distal end of the ultrasonic surgical instrument, and when the thumb pad actuator is pushed forward in a distal direction, the rotational clamp arm is opened relative to the stationary blade, and when the thumb pad actuator is pulled rearward in a proximal direction, the clamp arm is closed relative to the stationary blade.

2. An ultrasonic surgical instrument which is ergonomically designed to be comfortable and reduce fatigue in a surgeon operator's hand and arm, comprising:
   a. a housing body shroud for the ultrasonic surgical instrument which defines a handle which is held in the palm of a surgeon user to balance the weight of the instrument during usage;
   b. a thumb pad actuator translationally mounted on the upper surface of the body shroud for distal and proximal movements along substantially the same arc that the thumb naturally follows when bending proximally and distally at the first knuckle, thereby providing an actuating movement by the thumb along a familiar and natural arc which facilitates a coordinated easy actuation with very little major muscle movement;
   c. an ultrasonic waveguide for transferring ultrasonic vibrations to the distal end of the surgical instrument to perform a useful surgical procedure thereat;
   d. wherein a rotational coupler is rotationally mounted within the instrument housing to provide for complete rotational movement and freedom thereof within the surgical instrument.

3. The ultrasonic surgical instrument of claim 2, wherein a translationally-fixed, distal portion of the rotational coupler is rotationally mounted within the instrument housing by an annular retainer ring which is positioned between first and second annular collar retainers of the rotational coupler, to secure the distal portion of the rotational coupler within the housing against movements in a translational direction, while providing 360° angular rotational movement and freedom for the rotational coupler within the instrument housing.

4. The ultrasonic surgical instrument of claim 2, wherein an exterior rotational knob is positioned around and locked to the rotational coupler, such that the rotational knob can be rotated by the surgeon operator to rotate the rotational coupler and an attached angularly-extending clamp arm and angularly-extending blade relative to the surgical instrument.

5. The ultrasonic surgical instrument of claim 2, wherein an outer support tube is fixedly mounted to a translationally-fixed distal portion of the rotational coupler, and an inner actuating tube is mounted to a translationally-movable proximal end of the rotational coupler for limited distal and proximal translational movement within the outer support tube, to couple an actuating translating movement of the thumb pad actuator to an actuating rotational movement of a clamp arm relative to a blade at a stationary distal end of the surgical instrument.

6. The ultrasonic surgical instrument of claim 5, wherein the translationally-movable proximal portion of the rotational coupler is positioned around and secured to the proximal end of the inner actuating tube.

7. The ultrasonic surgical instrument of claim 6, wherein the translationally-movable proximal portion of the rotational coupler includes a plurality of longitudinally extending prongs which mount around and surround the proximal end of the inner actuating tube, securing the two components together for common rotational and translational movements.

8. The ultrasonic surgical instrument of claim 2, wherein the thumb-pad actuator extends downwardly at its distal end in a wishbone construction having downwardly-depending, spaced-apart resilient wishbone legs, each of which supports an inwardly projecting drive pin, which pins are positioned on opposite sides of a tubular collar which is mounted around the translationally-movable proximal portion of the rotational coupler which is mounted for limited distal and proximal translational movements relative to the translationally-fixed distal portion of the rotational coupler.

9. The ultrasonic surgical instrument of claim 8, wherein the tubular collar includes first and second spaced annular collar retainers which extend circumferentially around the rotational coupler, and a series of ridged detents is defined between the first and second collar retainers which extend circumferentially around the rotational coupler to provide a positive detent action against the resiliently mounted drive pins during rotation of the rotational coupler.

10. The ultrasonic surgical instrument of claim 9, wherein a pin extends through diametrically-opposed holes in a cylindrical sleeve of the translationally-fixed distal portion of the rotational coupler, through aligned diametrically-opposed holes in the proximal end of the outer support tube, and also through aligned longitudinally-extending, diametrically-opposed slots near the proximal end of the inner actuating tube, such that the cylindrical sleeve and the outer support tube are locked together by the pin for common rotational movement, and translational movements of the tubular collar caused by actuation of the thumb pad actuator result limited translational movement of the inner drive tube, with the elongated slot moving relative to the pin until the pin contacts ends of the elongated slots, and the translational movements of the inner tube within the outer support tube open or close the rotationally-mounted clamp arm relative to the end blade which is fixedly mounted to the distal end of the outer support tube.

11. The ultrasonic surgical instrument of claim 2, wherein Belleville washer springs are mounted at the proximal end of the rotational coupler to absorb an extra force applied to the thumb pad actuator, with the Belleville washer springs being compressed after the clamp arm is closed against the blade.

12. The ultrasonic surgical instrument of claim 5, wherein inwardly-projecting, diametrically-opposed pivot mount pins on the moveable clamp arm are rotationally mounted within diametrically-opposed apertures on opposite sides of the distal end of the outer tube, to rotate the clamp arm relative to the blade which is fixedly mounted at the distal end of the outer support tube.

13. The ultrasonic surgical instrument of claim 12, wherein inwardly-projecting, diametrically-opposed pivot legs on the moveable clamp arm are rotationally mounted within diametrically-opposed slots on opposite sides of the distal end of the inner actuating tube, to rotate the clamp arm relative to the blade which is fixedly mounted at the distal end of the outer support tube.

14. An ultrasonic surgical instrument which is ergonomically designed to be comfortable and reduce fatigue in a surgeon operator's hand and arm, comprising:
   a. a housing body shroud for the ultrasonic surgical instrument which defines a handle which is held in the palm of a surgeon user to balance the weight of the instrument during usage;
   b. a thumb pad actuator translationally mounted on the upper surface of the body shroud for distal and proximal movements along substantially the same arc that the thumb naturally follows when bending proximally and distally at the first knuckle, thereby providing an actuating movement by the thumb along a familiar and natural arc which facilitates a coordinated easy actuation with very little major muscle movement;
   c. an ultrasonic waveguide for transferring ultrasonic vibrations to the distal end of the surgical instrument to perform a useful surgical procedure thereat;
   d. wherein the upper central surface of thumb pad actuator has a horizontal S shaped design which fits the normal curvature of the thumb to provide greater comfort and control, and the upper surface also has a ribbed texturing to prevent thumb slippage.

15. A surgical instrument which is ergonomically designed to be comfortable and reduce fatigue in a surgeon operator's hand and arm, comprising:
   a. a housing body shroud for the surgical instrument which defines a handle which is held in the palm of a surgeon user to balance the weight of the instrument during usage;
   b. a thumb pad actuator translationally mounted on the upper surface of the body shroud for distal and proximal movements along substantially the same arc that the thumb naturally follows when bending proximally and distally at the first knuckle, thereby providing an actuating movement by the thumb along a familiar and natural arc which facilitates a coordinated easy actuation with very little major muscle movement;
   c. a rotational coupler rotationally mounted within the instrument housing to provide for complete rotational movement and freedom thereof within the surgical instrument.

16. The surgical instrument of claim 15, wherein a clamp arm is rotationally mounted relative to a blade which is stationarily supported at the distal end of the surgical instrument, and when the thumb pad actuator is pushed forward in a distal direction, the rotational clamp arm is opened relative to the stationary blade, and when the thumb pad actuator is pulled rearward in a proximal direction, the clamp arm is closed relative to the stationary blade.

17. The surgical instrument of claim 15, wherein a translationally-fixed, distal portion of the rotational coupler is rotationally mounted within the instrument housing by an annular retainer ring which is positioned between first and second annular collar retainers of the rotational coupler, to secure the distal portion of the rotational coupler within the housing against movements in a translational direction, while providing 360° angular rotational movement and freedom for the rotational coupler within the instrument housing.

18. The surgical instrument of claim 15, wherein an exterior rotational knob is positioned around and locked to the rotational coupler, such that the rotational knob can be rotated by the surgeon operator to rotate the rotational coupler and an attached angularly-extending clamp arm and angularly-extending blade relative to the surgical instrument.

19. The surgical instrument of claim 15, wherein an outer support tube is fixedly mounted to a translationally-fixed distal portion of the rotational coupler, and an inner actuating tube is mounted to a translationally-movable proximal end of the rotational coupler for limited distal and proximal translational movement within the outer support tube, to couple an actuating translating movement of the thumb pad actuator to an actuating rotational movement of a clamp arm relative to a blade at a stationary distal end of the surgical instrument.

20. The surgical instrument of claim 19, wherein the translationally-movable proximal portion of the rotational coupler is positioned around and secured to the proximal end of the inner actuating tube.

21. The surgical instrument of claim 20, wherein the translationally-movable proximal portion of the rotational coupler includes a plurality of longitudinally extending prongs which mount around and surround the proximal end of the inner actuating tube, securing the two components together for common rotational and translational movements.

22. The surgical instrument of claim 15, wherein the thumb-pad actuator extends downwardly at its distal end in a wishbone construction having downwardly-depending, spaced-apart resilient wishbone legs, each of which supports an inwardly projecting drive pin which are positioned on opposite sides of a tubular collar which is mounted around the translationally-movable proximal portion of the rotational coupler, which is mounted for limited distal and proximal translational movements relative to the translationally-fixed distal portion of the rotational coupler.

23. The surgical instrument of claim 22, wherein the tubular collar includes first and second spaced annular collar retainers which extend circumferentially around the rotational coupler, and a series of ridged detents is defined between the first and second collar retainers which extend circumferentially around the rotational coupler to provide a positive detent action against the resiliently mounted drive pins during rotation of the rotational coupler.

24. The surgical instrument of claim 23, wherein a pin extends through diametrically-opposed holes in a cylindrical sleeve of the translationally-fixed distal portion of the rotational coupler, through aligned diametrically-opposed holes in the proximal end of the outer support tube, and also through aligned longitudinally-extending, diametrically-opposed slots near the proximal end of the inner actuating tube, such that the cylindrical sleeve and the outer support tube are locked together by the pin for common rotational movement, and translational movements of the tubular collar caused by actuation of the thumb pad actuator result in limited translational movement of the inner drive tube, with the elongated slot moving relative to the pin until the ends of the elongated slots contact the pin, and the translational movements of the inner tube within the outer support tube open or close the rotationally-mounted clamp arm relative to the end blade which is fixedly mounted to the distal end of the outer support tube.

25. The surgical instrument of claim 15, wherein Belleville washer springs are mounted at the proximal end of the rotational coupler to absorb an extra force and movement applied to the thumb pad actuator, with the Belleville washer springs being compressed after the clamp arm is closed against the blade.

26. The surgical instrument of claim 19, wherein inwardly-projecting, diametrically-opposed pivot mount pins on the moveable clamp arm are rotationally mounted within diametrically-opposed apertures on opposite sides of the distal end of the outer tube, to rotate the clamp arm relative to the blade which is fixedly mounted at the distal end of the outer support tube.

27. The ultrasonic surgical instrument of claim 26, wherein inwardly-projecting, diametrically-opposed pivot legs on the moveable clamp arm are rotationally mounted within diametrically-opposed slots on opposite sides of the distal end of the inner actuating tube, to rotate the clamp arm relative to the blade which is fixedly mounted at the distal end of the outer support tube.

28. The surgical instrument of claim 17, wherein the upper central surface of thumb pad actuator has a horizontal S shaped design which fits the normal curvature of the thumb to provide greater comfort and control, and the upper surface also has a ribbed texturing to prevent thumb slippage.

29. The surgical instrument of claim 15, wherein the thumb-pad actuator is mounted on top of the surgical instrument for distal and proximal movements by first and second slide pins which are mounted for distal and proximal movements in first and second slide grooves defined in opposed body half shrouds of the surgical instrument, the first slide pin is mounted on the distal end of the thumb pad actuating, and the second slide pin is mounted on the proximal end of the thumb pad actuator, and the first slide groove extends distally and proximally in a generally horizontal direction, and the second slide groove extends distally and proximally in both a generally horizontal direction and also a rearward-downwardly extending direction, such that movement of the thumb pad actuator as guided by the first and second slide grooves follows the natural movement of an extending and retracting thumb of a surgeon operator.

30. A surgical instrument which is ergonomically designed to be comfortable and reduce fatigue in a surgeon operator's hand and arm, comprising:
   a. a housing body shroud for the surgical instrument which defines a handle which is held in the palm of a surgeon user to balance the weight of the instrument during usage;
   b. a thumb pad actuator translationally mounted on the upper surface of the body shroud for distal and proximal movements along substantially the same arc that the thumb naturally follows when bending proximally and distally at the first knuckle, thereby providing an actuating movement by the thumb along a familiar and natural arc which facilitates a coordinated easy actuation with very little major muscle movement;
   c. a surgical tip at the distal end of the surgical instrument for performing a useful surgical procedure thereat;
   d. wherein a clamp arm is rotationally mounted relative to a blade which is stationarily supported at the distal end of the surgical instrument, and when the thumb pad actuator is pushed forward in a distal direction, the rotational clamp arm is opened relative to the stationary blade, and when the thumb pad actuator is pulled rearward in a proximal direction, the clamp arm is closed relative to the stationary blade.

31. A surgical instrument which is ergonomically designed to be comfortable and reduce fatigue in a surgeon operator's hand and arm, comprising:
   a. a housing body shroud for the surgical instrument which defines a handle which is held in the palm of a surgeon user to balance the weight of the instrument during usage;

b. a thumb pad actuator translationally mounted on the upper surface of the body shroud for distal and proximal movements along substantially the same arc that the thumb naturally follows when bending proximally and distally at the first knuckle, thereby providing an actuating movement by the thumb along a familiar and natural arc which facilitates a coordinated easy actuation with very little major muscle movement;

c. a surgical tip at the distal end of the surgical instrument for performing a useful surgical procedure thereat;

d. wherein a rotational coupler is rotationally mounted within the instrument housing to provide for complete rotational movement and freedom thereof within the surgical instrument.

32. The surgical instrument of claim 31, wherein a translationally-fixed, distal portion of the rotational coupler is rotationally mounted within the instrument housing by an annular retainer ring which is positioned between first and second annular collar retainers of the rotational coupler, to secure the distal portion of the rotational coupler within the housing against movements in a translational direction, while providing 360° angular rotational movement and freedom for the rotational coupler within the instrument housing.

33. The surgical instrument of claim 31, wherein an exterior rotational knob is positioned around and locked to the rotational coupler, such that the rotational knob can be rotated by the surgeon operator to rotate the rotational coupler and an attached angularly-extending clamp arm and angularly-extending blade relative to the surgical instrument.

34. The surgical instrument of claim 31, wherein an outer support tube is fixedly mounted to a translationally-fixed distal portion of the rotational coupler, and an inner actuating tube is mounted to a translationally-movable proximal end of the rotational coupler for limited distal and proximal translational movement within the outer support tube, to couple an actuating translating movement of the thumb pad actuator to an actuating rotational movement of a clamp arm relative to a blade at a stationary distal end of the surgical instrument.

35. The surgical instrument of claim 34, wherein the translationally-movable proximal portion of the rotational coupler is positioned around and secured to the proximal end of the inner actuating tube.

36. The surgical instrument of claim 35, wherein the translationally-movable proximal portion of the rotational coupler includes a plurality of longitudinally extending prongs which mount around and surround the proximal end of the inner actuating tube, securing the two components together for common rotational and translational movements.

37. The surgical instrument of claim 31, wherein the thumb-pad actuator extends downwardly at its distal end in a wishbone construction having downwardly-depending, spaced-apart resilient wishbone legs, each of which supports an inwardly projecting drive pin, which pins are positioned on opposite sides of a tubular collar which is mounted around the translationally-movable proximal portion of the rotational coupler which is mounted for limited distal and proximal translational movements relative to the translationally-fixed distal portion of the rotational coupler.

38. The surgical instrument of claim 37, wherein the tubular collar includes first and second spaced annular collar retainers which extend circumferentially around the rotational coupler, and a series of ridged detents is defined between the first and second collar retainers which extend circumferentially around the rotational coupler to provide a positive detent action against the resiliently mounted drive pins during rotation of the rotational coupler.

39. The surgical instrument of claim 38, wherein a pin extends through diametrically-opposed holes in a cylindrical sleeve of the translationally-fixed distal portion of the rotational coupler, through aligned diametrically-opposed holes in the proximal end of the outer support tube, and also through aligned longitudinally-extending, diametrically-opposed slots near the proximal end of the inner actuating tube, such that the cylindrical sleeve and the outer support tube are locked together by the pin for common rotational movement, and translational movements of the tubular collar caused by actuation of the thumb pad actuator result limited translational movement of the inner drive tube, with the elongated slot moving relative to the pin until the pin contacts ends of the elongated slots, and the translational movements of the inner tube within the outer support tube open or close the rotationally-mounted clamp arm relative to the end blade which is fixedly mounted to the distal end of the outer support tube.

40. The surgical instrument of claim 31, wherein Belleville washer springs are mounted at the proximal end of the rotational coupler to absorb an extra force applied to the thumb pad actuator, with the Belleville washer springs being compressed after the clamp arm is closed against the blade.

41. The surgical instrument of claim 34, wherein inwardly-projecting, diametrically-opposed pivot mount pins on the moveable clamp arm are rotationally mounted within diametrically-opposed apertures on opposite sides of the distal end of the outer tube, to rotate the clamp arm relative to the blade which is fixedly mounted at the distal end of the outer support tube.

42. The surgical instrument of claim 41, wherein inwardly-projecting, diametrically-opposed pivot legs on the moveable clamp arm are rotationally mounted within diametrically-opposed slots on opposite sides of the distal end of the inner actuating tube, to rotate the clamp arm relative to the blade which is fixedly mounted at the distal end of the outer support tube.

43. A surgical instrument which is ergonomically designed to be comfortable and reduce fatigue in a surgeon operator's hand and arm, comprising:

a. a housing body shroud for the surgical instrument which defines a handle which is held in the palm of a surgeon user to balance the weight of the instrument during usage;

b. a thumb pad actuator translationally mounted on the upper surface of the body shroud for distal and proximal movements along substantially the same arc that the thumb naturally follows when bending proximally and distally at the first knuckle, thereby providing an actuating movement by the thumb along a familiar and natural arc which facilitates a coordinated easy actuation with very little major muscle movement;

c. a surgical tip at the distal end of the surgical instrument for performing a useful surgical procedure thereat;

d. wherein the upper central surface of thumb pad actuator has a horizontal S shaped design which fits the normal curvature of the thumb to provide greater comfort and control, and the upper surface also has a ribbed texturing to prevent thumb slippage.

44. A surgical instrument which is ergonomically designed to be comfortable and reduce fatigue in a surgeon operator's hand and arm, comprising:

a. a housing body shroud for the surgical instrument which defines a handle which is held in the palm of a surgeon user to balance the weight of the instrument during usage;

b. a thumb pad actuator translationally mounted on the upper surface of the body shroud for distal and proximal movements along substantially the same arc that the thumb naturally follows when bending proximally and distally at the first knuckle, thereby providing an actuating movement by the thumb along a familiar and natural arc which facilitates a coordinated easy actuation with very little major muscle movement;

c. a surgical tip at the distal end of the surgical instrument for performing a useful surgical procedure thereat;

d. wherein the thumb-pad actuator is mounted on top of the surgical instrument for distal and proximal movements by first and second slide pins which are mounted for distal and proximal movements in first and second slide grooves defined in opposed body half shrouds of the surgical instrument, the first slide pin is mounted on the distal end of the thumb pad actuating, and the second slide pin is mounted on the proximal end of the thumb pad actuator, and the first slide groove extends distally and proximally in a generally horizontal direction, and the second slide groove extends distally and proximally in both a generally horizontal direction and also a rearward-downwardly extending direction, such that movement of the thumb pad actuator as guided by the first and second slide grooves follows the natural movement of an extending and retracting thumb of a surgeon operator.

* * * * *